United States Patent
Petersen et al.

(10) Patent No.: US 7,309,590 B2
(45) Date of Patent: Dec. 18, 2007

(54) METHOD FOR PRODUCING AN AQUEOUS ACRYLAMIDE SOLUTION WITH A BIOCATALYST

(75) Inventors: Olaf Petersen, Meerbusch (DE); Burkhard Theis, Moers (DE); Michael Colberg, Willich (DE)

(73) Assignee: Ashland Licensing and Intellectual Property LLC, Dublin, OH (US)

( * ) Notice: Subject to any disclaimer, the term of this patent is extended or adjusted under 35 U.S.C. 154(b) by 462 days.

(21) Appl. No.: 10/475,100

(22) PCT Filed: Apr. 25, 2002

(86) PCT No.: PCT/EP02/04567

§ 371 (c)(1), (2), (4) Date: Mar. 31, 2004

(87) PCT Pub. No.: WO02/088373

PCT Pub. Date: Nov. 7, 2002

(65) Prior Publication Data

US 2004/0175809 A1    Sep. 9, 2004

(30) Foreign Application Priority Data

Apr. 26, 2001    (DE) ................ 101 20 550

(51) Int. Cl.
*C12P 13/02*    (2006.01)
(52) U.S. Cl. ...................... 435/129; 435/128
(58) Field of Classification Search ................ 435/128, 435/129
See application file for complete search history.

(56) References Cited

U.S. PATENT DOCUMENTS

| | | | |
|---|---|---|---|
| 4,181,576 A | 1/1980 | Malick et al. | |
| 4,414,331 A * | 11/1983 | Watanabe et al. | ........... 435/129 |
| 5,334,519 A | 8/1994 | Yamada et al. | |
| 5,604,132 A | 2/1997 | Capuano et al. | |
| 5,811,595 A | 9/1998 | Ellis | |
| 6,162,624 A | 12/2000 | Symes et al. | |

FOREIGN PATENT DOCUMENTS

| | | |
|---|---|---|
| DE | 30 17 005 | 4/1981 |
| DE | 30 22 912 | 6/1990 |
| DE | 44 80 132 | 3/1997 |
| EP | 0 188 316 | 10/1993 |
| EP | 1 046 706 | 10/2000 |
| GB | 2 054 563 | 2/1981 |
| RU | 2 112 804 | 6/1998 |
| WO | 01/57235 | 8/2001 |

OTHER PUBLICATIONS

The terms "preferable", "severe", and "excessive", Merriam-Webster Online Dictionary, at the web- http://www.m-w.com, pp. 1-3, Jan. 18, 2007.*
G. Stephanopoulos, (editor): "Biotechnology vol. 3, bioprocessing" VCH Verlagsgesellschaft, pp. 83 and 321-324 1993.
Jun Kik Hwang et al. Biotechnology and Bioengineering, vol. 34, pp. 380-386 1989.
Alan William Bunch Antonie Van Leeuwenhoek, vol. 74, pp. 89-97 1998.
Stanley M. Walas: "Chemical process equipment-selection and design" Butterworths Publishers, p. 45 1988.
U.S. Appl. No. 10/475,969, filed Oct. 27, 2003, Petersen.
U.S. Appl. No. 10/475,100, filed Oct. 27, 2003, Petersen et al.
U.S. Appl. No. 10/475,965, filed Oct. 27, 2003, Petersen et al.

* cited by examiner

*Primary Examiner*—Sandra E. Saucier
*Assistant Examiner*—Satyendra K. Singh
(74) *Attorney, Agent, or Firm*—Oblon, Spivak, McClelland, Maier & Neustadt, P.C.

(57) ABSTRACT

The invention relates to a method and device for producing an aqueous acrylamide solution by hydrating acrylonitrile in an aqueous solution while in the presence of a biocatalyst.

13 Claims, 1 Drawing Sheet

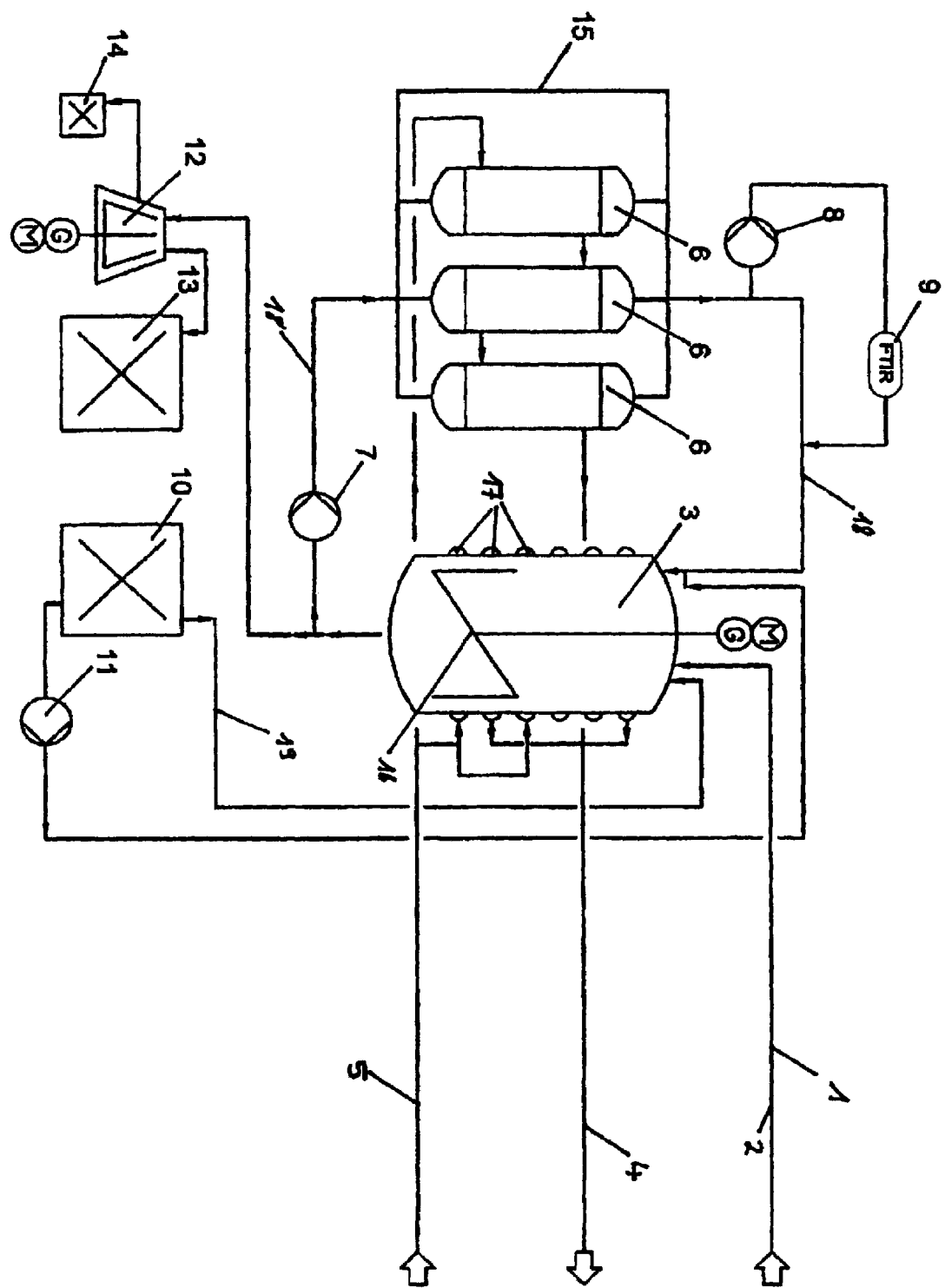

METHOD FOR PRODUCING AN AQUEOUS ACRYLAMIDE SOLUTION WITH A BIOCATALYST

The present invention relates to a method and a device for producing an aqueous acrylamide solution by hydrating acrylonitrile in an aqueous solution in the presence of a biocatalyst.

The conversion of acrylonitrile into acrylamide in the presence of a suitable biocatalyst in water has been known for many years and is described, for example, in DE 30 17 005 C2, whereby in this method the biocatalyst is immobilised. DE 44 80 132 C2 and EP 0 188 316 B1 describe special biocatalysts for the conversion of acrylonitrile into acrylamide. U.S. Pat. No. 5,334,519 teaches the hydration of acrylonitrile to form acrylamide in the presence of biocatalysts and cobalt ions. All these teachings have the drawback that the biocatalyst is damaged during the reaction so that its activity is reduced or there is an increased formation of undesirable by-products.

Therefore, it is the object of this invention to provide a method in which the biocatalyst is damaged as little as possible during the reaction, by-products are minimised and the batch time is optimised.

According to the invention, the object is achieved by a method for producing an aqueous acrylamide solution by hydrating acrylonitrile in an aqueous solution in the presence of a biocatalyst during which the reaction mixture is mixed, the reactor comprising a pumping circuit in which a part of the reaction mixture is circulated by means of a pump and in which at least one heat exchanger is arranged.

At the start of the reaction, deionised water and the biocatalyst are placed in the reactor and brought to a temperature of 15 to 25° C., preferably 16 to 20° C. When the temperature is reached, the acrylonitrile is added to the reactor and conversion to acrylamide commences. Preferably, the entire conversion takes places isothermally. At the start of reaction, the concentration of the biomass, expressed as solids, is preferably 0.03-2.5 g/l, particularly preferably 0.05-1 g/l and the pH value is preferably 6.0-8.0, particularly preferably 6.5-7.5.

Preferably, an agitating element with an intensive action is arranged in the reactor with which the reactor content is homogenously mixed. In a preferred embodiment, the reactor comprises external half-pipe coils with which the reaction mixture can be additionally cooled during the conversion of acrylonitrile into acrylamide.

According to the invention, the reactor has a pumping circuit in which a part of the reaction mixture is circulated by means of a pump. Arranged in this pumping circuit is at least one heat exchanger with which the reaction heat may be drawn off. Preferably, the heat exchanger is a shell-and-tube heat exchanger in which advantageously the reaction mixture is not diverted in order to avoid fouling on the heat exchanger surfaces.

In a preferred embodiment of the invention, the pump and the heat exchanger(s) are designed to ensure the avoidance of, on the one hand, temperature fluctuations in the reactor and, on the other, excessive energy input from the pump. Preferably, the pump is a magnetically coupled side channel pump.

Advantageously, the addition of the acrylonitrile to the pumping circuit is very particularly preferably performed directly before the re-entry of the reaction mixture into the reactor. The addition is preferably performed continuously.

A frequency-controlled piston-diaphragm pump has been found to be particularly advantageous as the feed pump for the acrylonitrile.

When the addition of the acrylonitrile is completed, a secondary reaction of preferably 4 to 20 minutes, particularly preferably 5 to 10 minutes, is required to convert the acrylonitrile as completely as possible. During this secondary reaction time, it is advantageous for the cooling to be successively reduced with the bypass.

To optimise the performance of the reaction, the course of the reaction in the reactor is advantageously monitored by means of on-line measurement. This measurement enables the performance of the reaction to be adapted very quickly in response to any possible changes. Preferably, the on-line measurement is performed in the pumping circuit before the acrylonitrile feed point and preferably, the acrylonitrile and/or the acrylamide concentration are continuously monitored.

On-line measurement with a Fourier transform infrared device (FT-IR device) has been found to be advantageous.

The results of the on-line measurement may be used to control the conversion. Advantageously, the quantity of acrylonitrile added, the volume of the pumped flow, the bypass volume and the secondary reaction time are controlled.

The method according to invention may be performed with any biocatalyst that catalyses the conversion of acrylonitrile into acrylamide. Preferably, however, the biocatalyst is a Rhodococcus rhodochrous depsited under the deposition number 14230 with DSMZ, Deutsche Sammlung von Mikroorganismen und Zellkulturen GmbH (German Collection of Microorganisms and Cell Cultures Ltd), Mascheroder Weg 1b, D-38124 Braunschweig, Germany.

The method according to the invention has the advantage that during the conversion of acrylonitrile into acrylamide, the biocatalyst is damaged as little as possible and therefore the quantity of biocatalyst to be used is minimised, fewer by-products are produced, the conversion of the acrylonitrile takes place at least almost completely and that an acrylamide solution of up to 50% by weight is achievable. The method according to the invention is simple and inexpensive to perform. The method according to the invention enables the reaction times to be drastically reduced. The biocatalyst is utilised to the optimum extent.

The method according to the invention is preferably performed in a device for the production of an aqueous acrylamide solution by hydrating acrylonitrile in an aqueous solution in the presence of a biocatalyst with a reactor, a pumping circuit in which a part of the reaction mixture is circulated by a pump and at least one heat exchanger arranged in the pumping circuit. Therefore, this device is a further subject of this invention.

Preferably, an agitating element with an intensive action is arranged in the reactor with which the content of the reactor is homogeneously mixed. In a preferred embodiment, the reactor comprises external half-pipe coils with which the reaction mixture may be additionally cooled during the conversion of acrylonitrile into acrylamide.

According to the invention, the reactor has a pumping circuit in which a part of the reaction mixture is circulated by means of a pump. Arranged in this pumping circuit is at least one heat exchanger with which the reaction heat may be drawn off. Preferably, the heat exchanger is a shell-and-tube heat exchanger in which the reaction mixture is advantageously not diverted in order to prevent fouling on the surfaces of the heat exchanger.

In a preferred embodiment of the invention, the pump and heat exchanger(s) are embodied to ensure the avoidance of, on the one hand, temperature fluctuations in the reactor and, on the other, excessive energy input from the pump. Preferably, the pump is a side channel pump.

Advantageously, very particularly preferably, the acrylonitrile is added to the pumping circuit directly before the re-entry of the reaction mixture into the reactor. The addition is preferably performed continuously. A frequency-controlled piston-diaphragm pump has been found to be particularly advantageous as the feed pump for the acrylonitrile.

When the acrylonitrile has been added, a secondary reaction of preferably 4 to 20 minutes, particularly preferably 5 to 10 minutes, is required to convert the acrylonitrile as completely as possible. During the secondary reaction time, it is advantageous for the cooling to be successively reduced with at least one bypass.

To optimise the performance of the reaction, the course of the reaction in the reactor is advantageously monitored by means of an on-line measurement. This measurement enables the performance of the reaction to be adapted very quickly in response to any possible changes. Preferably, the on-line measurement is performed in the pumping circuit before the acrylonitrile feed point and preferably, the acrylonitrile and/or the acrylamide concentration are continuously monitored.

On-line measurement with a Fourier transform infrared device (FT-IR device) has been found to be advantageous.

The results of the on-line measurement may be used to control the conversion. Advantageously, the quantity of acrylonitrile added, the volume of the pumped flow, the bypass volume and the secondary reaction time are controlled.

The device according to the invention has the advantage that during the conversion of acrylonitrile into acrylamide, the biocatalyst is damaged as little as possible and therefore the quantity of biocatalyst to be used is minimised, fewer by-products are produced, the conversion of the acrylonitrile takes place at least almost completely and that an acrylamide solution of up to 50% by weight is achievable. The device according to the invention is simple and inexpensive to operate. The method according to the invention enables the reaction times to be drastically reduced. The biocatalyst is utilised to the optimum extent.

The invention will be further described with reference to FIG. 1. However, these explanations are by way of example only and do not restrict the general concept of the invention.

FIG. 1 is a schematic diagram of the method according to the invention or parts of the device according to the invention. Before the start of the actual conversion of acrylonitrile into acrylamide, deionised water 1 and a suspension 2, containing the biocatalyst, are placed in the reactor 3. The content of the reactor 3 is mixed homogenously with a motor-driven agitator 16. On the exterior of the reactor 3 there are cooling coils 17 which are connected to the cold water inlet 5 and the cold water outlet 4. A person skilled in the art will recognise that these cooling coils can also be used to heat the reactor content to a specific temperature before the start of the actual reaction.

In addition, the reactor 3 comprises a pumping circuit 18 through which a part of the reactor content is circulated by means of the magnetically coupled side channel pump 7. Arranged in the pumping circuit 18 are three shell-and-tube heat exchangers 6 connected in parallel with which the reactor content may be heated or cooled. The heat exchangers 6 are also connected in series to the cold water inlet or outlet. In addition, the pumping circuit comprises the bypass 15 with which the heat exchanger 6 may be bypassed. The corresponding valves are not shown. The pumping circuit also contains the Fourier transform infrared device (FT-IR device) 9 for the on-line measurement of the acrylonitrile and acrylamide concentration in the circulated flow 18 and hence in the reactor 3. The sample flow is taken from the pumping circuit 18 and sent by means of the piston-diaphragm pump 8 to the FT-IR device 9 where it is analysed. The analytical data are used to control the method. Shortly before the pumping circuit 18 re-enters the reactor 3, the acrylonitrile to be converted is added thereto from the acrylonitrile receiver 10 by means of the diaphragm-feed pump 11. The acrylonitrile receiver 10 and the reactor 3 are connected to each other by means of a pendulum line 19 at the gas side. The line 19 is opened before the addition of the acrylonitrile commences and closed again when the addition is completed. When the reaction has finished, the aqueous acrylamide is separated from the biomass by means of an annular gap centrifuge 12 and the aqueous acrylamide collected in the receiver 13 and the biomass in the receiver 14.

The invention claimed is:

1. A method for producing an aqueous acrylamide solution, comprising:

forming a first mixture by mixing water and a biocatalyst in a reactor;

circulating the first mixture through the reactor and a pumping circuit with a pump, wherein the pumping circuit has at least one heat exchanger and a circuit with which said heat exchanger may be bypassed;

continuously adding acrylonitrile to the first mixture circulating through the pumping circuit and the reactor at a location after the heat exchanger and directly before the reactor to form a reaction mixture;

allowing the formation of acrylamide in said reaction mixture by the biocatalyst that catalyzes the conversion of acrylonitrile and water into the aqueous acrylamide solution;

cooling the reaction mixture by circulating the reaction mixture through the reactor and said pumping circuit; and monitoring the course of the reaction by on-line measuring at least one of the acrylonitrile and acrylamide concentration flowing through the pumping circuit at a location before the addition of the acrylonitrile to the pumping circuit.

2. The method according to claim 1, wherein the heat exchanger comprises external half-pipe coils.

3. The method according to claim 1, wherein the heat exchanger is a shell-and-tube heat exchanger.

4. The method according to claim 1, wherein the pump is a side channel pump.

5. The method according to claim 1, wherein the acrylonitrile is added to the first mixture with a frequency-controlled piston-diaphragm pump.

6. The method according to claim 1, wherein the first mixture is brought to a temperature of from 15 to 25° C. before adding the acrylonitrile to said first mixture.

7. The method according to claim 1, further comprising regulating the cooling of the reaction mixture by the heat exchanger by flowing the reaction mixture through the bypass after the acrylonitrile addition is completed.

8. The method according to claim 1, further comprising allowing the reaction to proceed for from 4 to 20 minutes after the acrylonitrile addition is completed.

9. The method according to claim 1, further comprising allowing the reaction to proceed for from 5 to 10 minutes after the acrylonitrile addition is completed.

10. The method according to claim 1, wherein the on-line measuring is carried out with a Fourier transform infrared (FT-IR) device.

11. The method according to claim 1, further comprising controlling the course of reaction based on said on-line measurement.

12. The method according to claim 11, wherein at least one of (i) the amount of acrylonitrile added, (ii) the flow through the pumping circuit, (iii) the flow through the bypass, and (iv) a secondary reaction time, are controlled.

13. The method according to claim 1, wherein the biocatalyst is *Rhodococcus rhodochrous*, Deposit No. 14230 at DSMZ, Deutshe Sammlung von Mikroorganismen und Zellkulturen GmbH, Mashroder Weg 1B, D-38124 Braunshwig, Germany.

* * * * *